United States Patent [19]
Telfair et al.

[11] Patent Number: 6,090,102
[45] Date of Patent: *Jul. 18, 2000

[54] SHORT PULSE MID-INFRARED LASER SOURCE FOR SURGERY

[75] Inventors: William B. Telfair, San Jose; Hanna J. Hoffman, Palo Alto, both of Calif.

[73] Assignee: IRVision, Inc., San Jose, Calif.

[ * ] Notice: This patent is subject to a terminal disclaimer.

[21] Appl. No.: 08/854,565

[22] Filed: May 12, 1997

[51] Int. Cl.$^7$ .................................................. A61B 18/180
[52] U.S. Cl. .................................... 606/10; 606/4; 606/3; 606/5
[58] Field of Search .................................. 606/2, 3, 4, 5, 606/6, 10, 11, 12, 13, 14, 15; 372/25, 26

[56] References Cited

U.S. PATENT DOCUMENTS

| | | |
|---|---|---|
| 3,564,450 | 2/1971 | Immarco et al. ................... 331/94.5 |
| 4,169,663 | 10/1979 | Murr . |
| 4,461,294 | 7/1984 | Baron . |
| 4,665,913 | 5/1987 | L'Esperance, Jr. . |
| 4,669,466 | 6/1987 | L'Esperance . |
| 4,720,189 | 1/1988 | Heynen et al. . |

(List continued on next page.)

FOREIGN PATENT DOCUMENTS

| | | |
|---|---|---|
| 0 279 589 | 8/1988 | European Pat. Off. . |
| 0 602 756 | 6/1994 | European Pat. Off. . |
| 0770370 A2 | 5/1997 | European Pat. Off. . |
| 2 622 426 | 10/1988 | France . |
| 35 40 763 | 5/1987 | Germany . |
| 42 32 915 | 4/1994 | Germany . |
| 93/14817 | 8/1993 | WIPO . |
| 94/18883 | 9/1994 | WIPO . |
| 95/27453 | 10/1995 | WIPO . |
| WO 96/33538 | 10/1996 | WIPO . |

OTHER PUBLICATIONS

Frenz, et al., "Comparison of the Effects of Absorption Coefficient and Pulse Duration of 2.12–$\mu$m and 2.79–$\mu$m Radiation on Laser Ablation of Tissue," IEEE Journal of Quantum Electronics, vol. 32, No. 12, Dec. 1996, pp. 2025–2036.

Pollnau, et al., "Investigation of Diode–pumped 2.8–$\mu$m Laser Performance in Er:BAy$_2$F$_8$," Optics Letters, vol. 21, No. 1, Jan. 1, 1996, pp. 48–50.

Könz, et al., "Active and Passive Q–Switching of a 2.79 $\mu$m Er:Cr:YSGG Laser," Optics Communications 103, Dec. 1, 1993, No. 5/6, pp. 398–404.

International Search Report, PCT/US98/01386, May 8, 1998, 3 pages.

Abel, T., et al., "Hollow Glass Waveguides for Broadband Infrared Transmission," Optics Letters, 19, 1034–1036 (1996).

Bende, T., et al., "Photoablatin in different ocular tissues performed with an erbium:YAG laser," Lasers in Opthalmology, 2, 263–269 91989).

Jacques, S. L., "Laser–Tissue Interactions: Photochemical, Photothermal, and Photomechanical," Lasers in General Surgery, 72(3), 531–558 (1992).

(List continued on next page.)

*Primary Examiner*—Linda C. M. Dvorak
*Assistant Examiner*—Sonya Harris-Ogugua
*Attorney, Agent, or Firm*—Cummings & Lockwood

[57] ABSTRACT

A solid state laser source for surgical applications which produces short-pulse, mid-infrared radiation. Specifically, the laser preferably emits radiation near the absorption peak of water, with energy levels up to 20 mJ, pulse durations shorter than 50 ns and preferably shorter than 30 ns, with beam quality of less than 8 times the diffraction limit. The short pulses reduce unwanted thermal effects and changes in adjacent tissue to potentially sub-micron levels. The laser source produces pulse repetition rates in excess of 10 Hz when pumped by a flashlamp, but in a diode pumped embodiment, the repetition rate may exceed 30 Hz. Of particular interest is an erbium-doped YAG laser which is especially well suited to the needs of mid-infrared corneal ablation procedures for correcting refractive errors, when constructed according to principles disclosed by the invention.

51 Claims, 4 Drawing Sheets

U.S. PATENT DOCUMENTS

| | | |
|---|---|---|
| 4,732,148 | 3/1988 | L'Esperance, Jr. . |
| 4,896,015 | 1/1990 | Taboada et al. . |
| 4,907,586 | 3/1990 | Bille et al. . |
| 4,911,711 | 3/1990 | Telfair et al. . |
| 4,968,130 | 11/1990 | Hideshima et al. . |
| 5,001,716 | 3/1991 | Johnson et al. ............................ 372/10 |
| 5,102,409 | 4/1992 | Balgorod . |
| 5,102,410 | 4/1992 | Dressel ...................................... 606/15 |
| 5,108,388 | 4/1992 | Trokel . |
| 5,130,995 | 7/1992 | Grossman et al. ......................... 372/13 |
| 5,291,505 | 3/1994 | Nielsen ..................................... 372/38 |
| 5,324,282 | 6/1994 | Dodick ...................................... 606/15 |
| 5,349,590 | 9/1994 | Amirkhanian et al. . |
| 5,350,374 | 9/1994 | Smith . |
| 5,360,424 | 11/1994 | Klopotek . |
| 5,465,154 | 11/1995 | Levy ....................................... 365/382 |
| 5,474,548 | 12/1995 | Knopp et al. . |
| 5,520,679 | 5/1996 | Lin . |
| 5,593,606 | 1/1997 | Owen et al. ........................ 219/121.71 |
| 5,598,425 | 1/1997 | Jain et al. ................................. 372/18 |
| 5,611,946 | 3/1997 | Leong et al. .......................... 219/121.6 |
| 5,614,114 | 3/1997 | Owen ................................. 219/121.66 |
| 5,640,412 | 6/1997 | Reed ....................................... 372/100 |
| 5,642,370 | 6/1997 | Mitchell et al. .......................... 372/25 |
| 5,644,585 | 7/1997 | Mitchell et al. .......................... 372/25 |
| 5,741,247 | 4/1998 | Rizoiu ...................................... 606/10 |
| 5,742,634 | 4/1998 | Rieger et al. ............................. 372/25 |

OTHER PUBLICATIONS

Jean, B., M.D., Ph.D., et al., "Correction of Myopia with Er:YAG Laser Fundamental Mode Photorefractive Keratecomy," Journal of Refractive Surgery, vol. 11 (1995).

Lian, J. et al., "Effects of Er:YAg laser of different pulse widths on rabbit corneas," SPIE, vol. 2393, 160–166 (1995).

Lin, J.T., "Mini–Excimer Laser Corneal Reshaping Using A Scanning Device," SPIE Proceedings, vol. 2132, Medical Lasers & Systems III (1994).

Munnerlynn, C.R., et al., "PhotoRefractive Keratecomy: a technique for laser refractive surgery," J. Cataract Refract. Surg., 14(1): 46–52 (1988).

Pettit, G.H., et al., "Excimer laser ablation of the cornea," Optical Engineering, 34, 661–667 (1995).

Peyman, G.A., et al., "Corneal ablation in rabbits using an infrared (2.9 μm) erbium–YAG laser," Opthalmology, 96, 1160–1170 (1989).

Ren, Q., et al., "Laser Refractive Surgery; a review and current ststus," Optical Engineering, 34, 642–660 (1995).

Ren, Q., et al., "Ultraviolent Solid–state Laser (213 nm) PhotoRefractive Keratecomy," Opthalmology, 100, 12, 1828–1834 (1993).

Ren, Q., et al., "Mid–Infrared Laser Ablation of the Cornea: A Comparative Study", Lasers in Surgery and Medicine 12:274–281 (1992).

Ren, Q., et al.., "Axcion: A New Laser Beam Delivery System for Corneal Surgery", IEEE Journal of Quantum Electronics 26 (1990).

Seiler, T., et al., "Fundamental mode photoablation of the cornea for myopic correction," Lasers and Light in Opthalmology, 5, 4, 199–203 (1993).

Stern, David, et al., "Infrared Laser Surgery of the Cornea; Studies with a Raman–shifted Neodymium:YAG Laser at 2.80 and 2.93 μm," Opthamology, Oct. 1988, vol. 95, No. 10.

Walsh, J.T., et al., "Er:YAG laser ablation of tissues: effect of pulse duration and tissue type on thermal damage," Laser Surgical Medicine, 9, 314–346 (1989).

Wang, K., et al., "Comparison of Er: YAG and Excimer laser corneal ablation in rabbits," Lasers in Opthalmology, 6, 69–75 (1994).

Webb, R.H., et al., "Measurement of Ocular Local Wavefront Distortion with a Spatially Resolved Refractometer," Applied Optics, 31, 19, 3678–3686 (1992).

Derwent Abstracts for DE 35 40 763.

Derwent Abstract for DE 42 32 915.

Product brochure, Orbscan A Pan Corneal Slit Topography & Pachymetry System, Orbect, Salt Lake City, UT 84115 (undated).

Product Brochure, Visx Twenty Excimer Laser System, "Reshaping Vision," Alcon International, Alcon Laboratories, Inc., Fort Worth, TX 76134 (1992).

European Patent Office, "European Search Report", May 14, 1997, pp. 1–2.

European Patent Office, "Annex To The European Search Report", May 14, 1997, pp. 1–2.

Dingus, R.S. et al., "Gröneisen–stress induced ablation of biological tissue," SPIE vol. 1427 Laser–Tissue Interaction II (1991).

SHORT PULSE MID-INFRARED LASER SOURCE FOR SURGERY

FIELD OF THE INVENTION

The present invention relates to laser sources for surgical procedures, and more particularly, to a surgical laser apparatus which directly produces short-pulse, mid-infrared radiation.

BACKGROUND OF THE INVENTION

In recent years, there has been a surge of interest in erbium-doped solid state lasers emitting near 3 microns for medical procedures because radiation at this wavelength is strongly absorbed by water contained in biological tissue. In the absence of pigment, water acting as a chromophore largely determines the light absorption properties of the respective tissue. For example, the absorption coefficient of water around 3 μm is more than four orders of magnitude higher than the absorption near the common 1 μm wavelength, resulting in shallow penetration depths and highly localized interactions at these mid-infrared wavelengths.

One solid state laser in particular, the erbium-doped YAG (Er:YAG) laser, emits radiation at a wavelength of 2.94 μm, virtually at the peak of the water absorption curve. With an absorption coefficient of over 13000 cm$^{-1}$, this laser can produce a very small region of impact with potentially less than one or two microns penetration depth. Since the ablation threshold and extension of thermal injury are inversely proportional to the absorption coefficient, the Er:YAG's emission can be particularly effective in certain surgical applications including delicate endoscopic procedures, micro-ocular surgery and corneal sculpting, all of which require a high degree of precision and control combined with minimal damage to tissue adjacent to the surgical site.

One particular application generating growing interest in the past few years involves the procedure of photorefractive keratectomy (PRK) for reshaping the cornea of the eye. PRK techniques based on volumetric removal of tissue using ultraviolet (UV) radiation, typically from a 193 nm ArF excimer laser, have become widely utilized as an effective means for correcting visual deficiencies. At this short wavelength, the high photon energy causes direct breaking of intramolecular bonds, a process known as photochemical decomposition. Tissue ablation based on this photochemical mechanism has the advantage of producing minimal collateral thermal damage in cells adjacent to the surgical site. Also, the depth of decomposition is very small, typically less than 1 micron, resulting in accurate tissue removal with minimal risk of damage to underlying structures from the UV radiation.

While established by the Food and Drug Administration (FDA) in the United States as a safe and effective method of corneal ablation, excimer based methods also suffer from a number of deficiencies, including high initial and maintenance costs, large and complex optical beam delivery systems, safety hazards due to the fluorine and ozone gas formation and persistent reliability problems. Furthermore, the potential phototoxicity of high power UV radiation is still an undetermined risk in excimer-laser-based PRK. In particular, there is concern that the UV radiation poses certain mutagenic and cataractogenic risks due to secondary fluorescence effects.

Ablation at mid-infrared wavelengths using, especially radiation around 3 μm, has been suggested as an alternative to the excimer laser for performing corneal refractive surgery. With water being the main constituent of the cornea, radiation corresponding to the absorption peak of water has the potential to ablate tissue selectively with minimal collateral thermal damage, similar to what is produced with the excimer laser. The premise underlying interest in such an alternative system is that infrared radiation can be produced with an all-solid-state technology which would provide easier handling, be cheaper, more compact and have better reliability features, while eliminating the potential of any safety concerns due to toxic gases or mutagenic side effects associated with deep UV wavelengths. The fact that there was a solid state laser fortuitously emitting radiation with the desired wavelength, namely, the Er:YAG laser, contributed to the interest in exploiting a controlled thermal mechanism for this application.

Contrary to the photoablation mechanism associated with the excimer laser, i.e., photochemical decomposition, ablation in the infrared wavelength range is generally attributed to photothermal vaporization. This process inherently has a larger effect than photodecomposition, allowing for removal of up to several microns of tissue per pulse at a time, thereupon resulting in faster surgical operations, but also with a larger thermal damage zone. A system for performing PRK based on a photovaporization process has been suggested, for example, by T. Seiler and J. Wollensak, in "Fundamental Mode Photoablation of the Cornea for Myopic Correction", Lasers and Light in Ophthalmology, 5, 4, 199–203 (1993). Another system has been described by Cozean et al. in PCT Application No. 93/14817, which relies on a sculpting filter to control the amount of tissue removal using a pulsed 3 μm Er:YAG laser. However, while ophthalmic surgical techniques based on such free-running or long-pulse erbium lasers have shown some promise, they also suffer from a number of drawbacks principally relating to the fact that the IR radiation causes collateral thermal damage to tissue adjacent to the ablated region. In fact, the size of the damage zone with such systems may be up to 50 microns, leading to potentially undesirable short and long term healing side effects such as haze, regression, and loss of visual acuity.

Recently, it has been recognized that mid-infrared lasers emitting shorter pulses, for example, utilizing Q-switched lasers, cause less thermal damage. For a review of mid-infrared laser systems, see, for example, Q. Ren et al in Opt. Eng., 34, pp. 642–660, 1995. However, even with pulses this short, on the order of hundreds of nanoseconds, compared to hundreds of microseconds for previous studies, the collateral damage zone still extends up to 21 μm. See, for example, J. Lian & K. Wang in SPIE., 2393, pp. 160–166, 1995. Since such extended thermal damage zones are still accompanied by haze, regression, and other deleterious healing side-effects, this puts infrared lasers at a disadvantage when compared with excimer lasers for corneal ablation.

More recently, a direct tissue interaction effect known as photospallation, or photomechanical ablation, has been observed at infrared wavelengths, whereby, with pulses shorter than 50 nanoseconds and preferably shorter than 30 ns, radiation interacts exclusively with the irradiated tissue producing negligible effect upon the adjacent, unirradiated tissue. Photospallation is a photomechanical ablation mechanism (distinctly different from both photothermal vaporization and photochemical decomposition), resulting from the rapid absorption of incident radiation and subsequent expansion by the corneal tissue. This expansion is followed by a bi-polar shock wave which causes removal of tissue. This process was originally described in Jacques, S. L. "Laser-Tissue Interactions: Photochemical, Photothermal, and Photomechanical," Lasers in General Surgery, 72(3),531–558 (1992) and was recently observed in animal experiments conducted with short pulse mid-infrared scanning laser delivery systems constructed according to principles similar to those described in our U.S. patent application Ser. No. 08/549,385, which is incorporated by reference herein.

Generally, U.S. patent application Ser. No. 08/549,385 discloses a method and apparatus for performing corneal surgery utilizing a short-pulse (less than 50 ns) solid state laser emitting mid-infrared radiation, preferably at or around 2.94 μm, scanned over a region of the cornea to allow uniform irradiation of the treatment region using a relatively low-energy laser (less than 30 mJ). By taking advantage of the lower energy density threshold (defined as the lowest fluence at which ablation occurs) associated with the photo-spallation process, tissue would thus be removed more accurately and safely than with prior art methods and apparatus. As one example of such prior art, ablation thresholds ranging from 200 to 600 $mJ/cm^2$ were recited by J. T. Lin in U.S. Pat. No. 5,520,679 as necessary for corneal sculpting application at mid-infrared wavelengths, including 2.94 μm. It was pointed out in the Lin patent, that one possible laser source for this application would be an Er:YAG laser with output energy of over 50 mJ (and up to 500 mJ) and with pulse durations that are between 50 and 400 ns. By contrast, we have shown that considerably lower ablation fluence thresholds are possible with a pure photo-spallation mechanism which is exploited to best advantage when the pulse duration is shorter than 50 ns.

In our recent experiments, we determined that there is a significant dependence of ablation thresholds on the pulse duration and that thresholds lower than 100 $mJ/cm^2$ are consistently feasible with pulses shorter than 50 ns. The significance of this finding is that it is possible to carry out a corneal ablation procedure using a mid-infrared short pulse laser with much lower energy outputs than previously taught. For example, with a pulse duration shorter than 50 ns, energy of less than 1 mJ per pulse in a 1 mm diameter spot size delivered to the cornea is sufficient to produce consistent ablation. Assuming losses in the beam delivery system of around 50%, less than 2 mJ of laser output per pulse is needed.

As suggested in our U.S. patent application Ser. No. 08/549,385, a Q-switched erbium-doped laser, operating directly at 2.94 μm, becomes a practical option for such a laser source. A compact, reliable erbium laser has a number of desirable properties, including its simplicity of design, ease of maintenance and potentially low cost. While highly attractive, there were a number of factors which, to date, hindered the realization of an Er:YAG laser operating in the desired short pulse mode. In particular, it was believed that commercially available Q-switches based on Pockels cells with standard nonlinear materials such as $LiNbO_3$ (lithium niobate) may not be appropriate for erbium-doped lasers due to unacceptably high absorption in both material and coatings near the 3 μm wavelength, leading to low energy threshold for damage. On the other hand, alternative methods for Q-switching that rely on rotating prisms and mirrors, for example, those used by Lian & Wang in SPIE, 2393, pp. 160–166, 1995, or frustrated total internal reflection (FTIR), for example, as discussed by H. J. Eichler et al in Opt. Mat. 5, pp. 259–265, 1995 tended to result in pulse durations that were longer than 60 ns.

For the applications of interest, however, where ablation precision on the order of 1 micron are desired, a shorter pulse (shorter than 50 ns) is preferred, as such shorter pulses will increase the percentage of a true photospallative ablation process over a photothermal one, thus reducing residual contributions to tissue ablation from undesirable thermal effects to a minimum. It has been observed that an Er:YAG laser with the range of parameters taught by Lin will not result in the requisite sub-micron thermal effects and, hence, the shorter pulses recited above are important to achieving clinically successful ablation results in the mid-infrared region, similar to those of an excimer laser.

Due to limitations imposed by fundamental level dynamics and long upper-laser-level lifetimes, a practical lower limit on the pulse duration for a Q-switched erbium based laser is estimated to be about 20 ns. An electro-optic pulse switching means is, in principle, capable of achieving this pulse duration but has not yet been realized at useful energy output levels. For example, a lamp-pumped Er:YAG laser which was Q-switched electro-optically with a $LiNbO_3$-based modulator achieved only 7.5 mJ with pulse durations that were longer than 100 ns and at very low efficiency. For a more detailed discussion of such results, see, for example, E. Nava et al, SPIE vol. 2624, p. 246,1988. The main issue that prevented achievement of a higher energy and shorter pulse width in these experiments was damage to the optical components, including, but not limited to, the Q-switch material. While the FTIR Q-switch suggested by H. J. Eichler, as discussed above, may achieve a shorter pulse duration, on the order of 60 ns, it also limits the repetition rate to less than 10 Hertz, due to thermal loading and time constant characteristics.

The present invention discloses a novel approach to constructing an erbium-doped laser apparatus which overcomes the aforementioned difficulties and is capable of producing considerably shorter-pulse radiation with higher energy at or near 2.94 μm. The apparatus is uniquely suited to performing PRK reliably and at low cost, thus greatly increasing the availability of the procedure to a larger number of people. Furthermore, with certain adjustments to the apparatus, it may be used for other ophthalmic procedures where a concentrated pulsed beam at a selected mid-IR wavelength has demonstrated benefits, such as in laser sclerostomy, trabeculectomy and vitreo-retinal surgery. Several such procedures were described in our companion U.S. pat. application Ser. No. 08/549,385, all of which are incorporated by reference herein. The recent emergence of fiber delivery systems for delivering mid-IR wavelengths may also provide further utility for the erbium short pulse laser in general endoscopic microsurgical applications, including in neural, orthoscopic and spinal cord surgery. Such medical procedures may derive great benefit from the highly localized effects generated by variants of the present system because of the delicate nature of the tissues involved.

SUMMARY OF THE INVENTION

It is therefore an object of this invention to provide a new and improved surgical laser apparatus that is well adapted to performing delicate surgical operations, such as corneal refractive surgery and other micro-ocular and micro-surgical procedures. It is a particular object to facilitate a new and improved method of photorefractive laser surgery based on utilizing short-pulse, mid-infrared radiation produced by an erbium-doped laser.

The pulse duration is viewed as critical to reducing unwanted changes in adjacent tissue and especially thermal effects which can result in undesirable damaged tissue at the interaction site produced by the infrared radiation. In particular, for a PRK procedure with sufficiently short pulses, a photospallation mechanism is triggered, whereby tissue is removed primarily by photomechanical rather than photothermal means, thus allowing an operation to be performed at lower fluence levels than was possible heretofore. Consequently, the thermal damage is reduced to potentially sub-micron levels, resulting in the same, and possibly even better, clinical indications as ablative photochemical decomposition produced by deep-UV lasers, the primary method presently utilized in refractive laser surgery. Therefore, it is a key aspect of the present invention to provide a laser source with pulse durations shorter than 50 ns (and preferably shorter than 30 ns), at or near the 2.94-$\mu$m water absorption maximum.

It is thus a corresponding key object of this invention to provide a new and improved laser surgical apparatus utilizing a relatively low energy, short pulse Er:YAG laser which is most advantageously constructed using a simple optical configuration with a minimal number of optical elements placed in a short practical resonator. With such a configuration, optical losses are kept low and the risk of damage to optical element coatings is minimized thus allowing short pulses to be produced most efficiently and reliably.

According to another object, the laser cavity parameters are selected in order to accommodate readily available Er:YAG rods and an electro-optic Q-switch, while still producing stable output pulses, less than 50 ns (and preferably less than 30 ns) long at energy levels scaleable up to 20 millijoules and with repetition rates in excess of 10 Hz (and preferably greater than 30 Hz). In a preferred embodiment of the laser, the spatial output of the laser is single or multimode, with either a Gaussian or top-hat spatial profile. In addition, the divergence ranges to less than ten times the diffraction limit but preferably no larger than a few times the diffraction limit—depending upon tradeoffs with specifics of the optical system delivering the radiation to the operation site.

It is still another object to provide a new apparatus and method for performing refractive and other ophthalmic surgery using a novel construction of a diode-pumped erbium laser oscillator which would allow generation of pulses shorter than 30 ns at energies of up to 20 mJ and with repetition rates scaleable to over 50 Hz.

A more complete understanding of the present invention, as well as further features and advantages of the invention, will be obtained by reference to the detailed description and drawings following below.

DETAILED DESCRIPTION

A mid-IR laser source is disclosed with parameters selected to yield a beam with properties matched to optimize tissue removal based on a photospallation mechanism. Optimally, the laser beam comprises a series of discrete pulses with a wavelength at or near 2.94 $\mu$m, each less than 50 ns in duration (and preferably, less than 30 ns) and having energy of up to 20 mJ, emitted at repetition rates of at least 10 Hz, but scaleable to over 30 Hz. The higher repetition rates are desired in certain surgical applications, such as PRK, both to minimize the duration of the procedure, and to allow utilization of smaller spot sizes with better overlap parameters as needed in a scanning mode for improved surface smoothness of the surgical site.

The critical nature of the pulse duration is related to the threshold for a photospallation process, which becomes lower as the pulse duration decreases, as recently observed in our experiments. In particular, our data showed that with very short pulse durations from a 2.94 $\mu$m laser (less than 10 ns), energy density (or fluence) thresholds that are as low as 60 mJ/cm$^2$ were consistently achieved. Even with pulses that are about 70 ns long, produced by an Er:YAG laser, the thresholds were less than 100 mJ/cm$^2$. It was also found in the same experiments that generally, the longer the pulse, the larger is the thermal component of the radiation interaction with tissue, resulting in a corresponding increase in the damage zone.

It is therefore preferred that the erbium laser according to the present invention yields pulses that are shorter than 50 ns and preferably shorter than 30 ns, as stated above. In this case, energy levels of 10 mJ and below will be sufficient to produce effective ablation at 2.94 $\mu$m in corneal tissue, although up to 20 mJ may be required for other tissues. The combination of (i) lower total energy per pulse with lower fluence on the target tissue and (ii) lower percentage of the energy which is converted into heat dramatically reduces the thermal damage to the residual tissue at the surface of the ablation. Based on our data, we maintain that thermal damage zones as low as 0.5 $\mu$m but no larger than 2 $\mu$m, can be achieved with a short pulse erbium laser. The actual thermal damage zone will depend on the specific laser pulse duration and trade-offs between energy available from the laser, losses in the beam delivery system, spot sizes, spot overlap and available repetition rate. By comparison, ablation thresholds routinely achieved with prior art systems were in the range of 200 to 600 mJ/cm$^2$ and systems using this fluence caused at least 14 microns and, typically 10–20 $\mu$m of damage. The small damage zone of the short pulse laser associated with the present invention is, therefore, an important factor in producing highly localized ablation with clinical results similar to what is obtained currently with UV radiation from ArF excimer lasers, where sub-micron collateral damage zones have been demonstrated.

With the 193 nm radiation from an ArF excimer laser, for example, ablation thresholds are known to be about 60 mJ/cm$^2$ and typical clinical fluences are a factor of 2-to-4 times that, i.e., ranging from a low of 120 mJ/cm$^2$ to a high of 250 mJ/cm$^2$. Our recent data indicate that operational fluences required from a short pulse Er:YAG laser are similar to those produced with current excimer laser systems and will produce similarly successful ablation results, even though the ablation mechanism is different in the mid-IR from that in the UV (i.e., it is photomechanical spallation rather than a photochemical decomposition).

Figure 1:
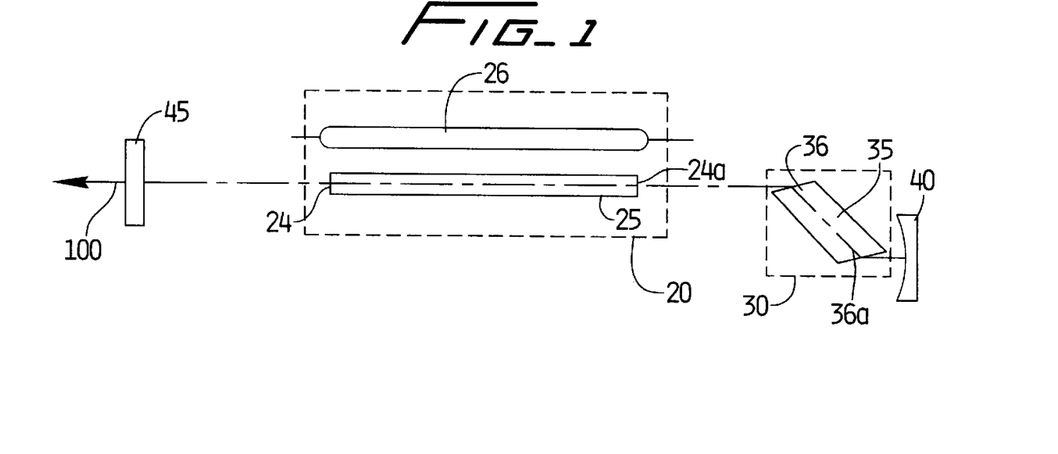
FIG. 1 is a schematic of a preferred optical configuration for a Q-switched Er:YAG laser according to the present invention using a flat-ended rod and a Brewster-cut Q-switch material.

Accordingly, disclosed in this invention is an efficient short pulse mid-infrared laser source comprising an Er:YAG laser oscillator which is Q-switched electro-optically, preferably using a standard Pockels cell with an available nonlinear crystal, yet without the propensity to damage that undermined prior art designs. Shown in FIG. 1 is an optical schematic of a preferred embodiment of the short-pulse Er:YAG laser oscillator including an optical head 20 containing the erbium-doped laser rod 25 pumped by flashlamp 26, a Pockels cell 30 containing an electro-optically active crystal 35, such as LiNbO$_3$, a high reflecting mirror 40 and an outcoupling mirror 45. The four optical elements shown in FIG. 1 preferably comprise the entire optical configuration of the laser. Since it is well known that degradation of optical surfaces due to water contamination and subsequent absorption of the beam poses a major reliability problem for 3 micron lasers, it is a key aspect of our approach to minimize the number of optical components in the resonator cavity, thus lowering the overall risk of damage to sensitive materials and coatings. Thus, it is preferred that no other optical components such as polarizers or hard apertures be included in the cavity.

An added advantage of the small number of optical elements is that the optical losses are reduced to the lowest possible level. This is an important consideration for operation at the relatively low gain levels typical of the short pulse, low energy Er:YAG laser that best matches the corneal ablation application requirements. Still another advantage of utilizing the fewest possible components is that very short cavity lengths can be practically realized. This is also a key factor in our approach to constructing an erbium laser that is uniquely adapted to the short-pulse application needs, as discussed below.

Specifically, short resonator lengths are regarded as critical to the formation of short pulse widths because the Er:YAG stored energy and gain are not very high in this application. Usually, the pulse duration becomes shorter as the gain increases but for our purposes, where only relatively low energy outputs are needed or desired, reliance on high gain to shorten the pulses represents a poor match to the required surgical device operating characteristics. Instead, short resonator lengths provide a preferred practical path to realization of short Q-switched pulses. With a short resonator, the cavity round trip time is minimized, thus the shortest pulses can be generated with the simplest cavity design. In the preferred embodiment, cavity lengths of 10-to-20 cm were determined to be compatible with pulse lengths from a low of 20 ns up to 50 ns in a Q-switched Er:YAG laser, depending on the specifics of pump energy density, pump light absorption efficiency and generated gain.

It is noted that thermal lensing considerations drive specific designs of the erbium resonator of FIG. 1. This is especially true for erbium lasers which are known to possess a strong thermal lens, the effect of which gets stronger still as the repetition rate increases. Thus, thermal lensing is the determining factor in establishing the cavity overall power, and the fundamental TEM$_{00}$ mode dimensions at a particular repetition frequency. For each given rod aperture, the TEM$_{00}$ mode diameter, determines, in turn, the divergence of the output beam from the laser. Generally, because of the relatively long 3 micron wavelength of the laser, TEM$_{00}$ diameters tend to be larger than those associated with other solid state lasers (such as, e.g., 1 micron neodymium-doped YAG lasers). This is offset by the stronger thermal lensing which tends to shrink the beam, resulting in smaller mode diameters and driving the design towards multimode operation. In one preferred embodiment of a resonator built according to the principles embodied in FIG. 1, standard laser calculations show that, for a short resonator length on the order of 10 cm, a rear reflector 40 of 1 m curvature, the fundamental mode dimensions range from about 0.6-to-1 mm in diameter over a fairly wide range of thermal focal lengths values which are smaller than 1 m. This was found to be typical for repetition rates of about 5–10 Hz.

At higher repetition frequencies (>10 Hz), the rod's thermal lens power is even more dominant in establishing the cavity overall power and hence the TEM$_{00}$ mode dimensions. Furthermore, the situation for higher repetition rates becomes more complicated due to thermal birefringence effects manifested in increased divergence and spatial beam profiles that become progressively less symmetric as the heat load in the laser material increases. Divergence subsequently impacts the dimensions of the imaging optics used to transport the beam out of the laser to the target, for example, the eye. There is thus a trade-off between the repetition rate and the beam's spatial profile which is a particularly important design consideration for an Er:YAG laser used as a source for delivering a beam with a specific spot size and energy distribution.

Taking all these considerations into account, we determined that in one practical embodiment, selecting an output coupling mirror 45 reflecting 75% of the light, a 1 m high reflectivity mirror 45 and a 3–4 mm diameter rod were adequate to provide Q-switched energies of over 15 mJ with only 30 J input energy from the lamp at 10 Hz with divergence of less than 8 times the diffraction limit and acceptable beam profile characteristics. The pulse duration for such a resonator could be varied from as low as 30 ns to over 50 ns, depending only on the cavity length, with the lower limit set by risk of damage to the Q-switch material and/or the rod's coatings when intracavity power densities become overly high. We also determined that repetition rates for an Er:YAG laser with this range of parameters could be scaled up to 20 Hz with appropriate design improvements, at a cost of some increase in the beam divergence.

As noted above the physically short resonator gives rise to small fundamental mode dimensions (as compared with the rod's limiting aperture). These may be reduced further in the presence of thermal lensing in the laser material. To operate the laser as a fundamental transverse mode device would require intracavity aperturing to very small beam diameters rendering much of the stored laser rod energy inaccessible and yielding poor overall efficiencies. To achieve reasonably uniform transverse beam profiles without fundamental mode operation, it is preferable to engage a high number of transverse modes. The resultant mode overlap and mixing can provide an approximately flat-topped beam that is well suited to illumination and imaging applications such as those contemplated herein. This mode of operation has the added attribute of high cavity stability, as well as advantages in alignment and maintenance.

In the preferred embodiment of FIG. 1, the Er:YAG rod 25 is fabricated with flat ends 24, 24a while the nonlinear Q-switch material 35 is shown as cut at the preferred Brewster angle. This configuration serves three purposes: the Brewster angles on the modulating crystal provide the polarizing surface necessary for Q-switching, the damage prone AR-coating on the nonlinear crystal can be eliminated and the required retardation voltage is smaller. In addition, the flat faces 24, 24a of the rod 25, which constitute the generated laser beam's limiting aperture, lead to a circular beam output profile that is well suited to a scanning delivery system as well as to most of the applications contemplated which typically involve remote imaging of the beam on a target. A flat rod also allows relatively small diameters to be utilized which helps maximize the gain-per-unit stored energy. Preferably, the rod has a diameter of less than 4 mm but care must be taken to ensure that the diameter is not so small as to risk damage to this critical component in the short pulse operating mode. The length of the laser rod is then determined based on standard design criteria for optimizing the lamp-to-rod aspect ratio, coupled with optical loss considerations. In a preferred embodiment, rod diameters of 2–4 mm and lengths between 70 and 90 mm are adequate dimensions to match to the range of operating parameters considered herein.

The erbium concentration is another important aspect of the Er:YAG gain material. Standard rods have erbium doping concentrations of about 50%. Such high doping levels are considered optimal for high power, long pulse erbium lasers, by providing strong broadband absorption of pump light, thus contributing to increased laser efficiency. In such long pulse erbium lasers, lasing tends to begin during the lamp pump pulse once sufficient gain is achieved to overcome the threshold as determined by cavity losses. Most such non-switched devices operate at moderate to high pump and output energy levels. In this mode of operation, the contributions associated with increased concentration are largely positive. However, for the present applications, where short pulses at considerably lower energies are desired, lower doping levels may be more optimal. One reason is that in the contemplated Q-switched operational mode, the pump energies employed are typically much lower, and there may be insufficient energy to elevate all portions of the rod's aperture above threshold. In effect, the beam intensity at the rod's center can be so low as to not reach the threshold for inversion. Thus, the strong pump absorption associated with high active ion concentrations can result in the pump light absorbed more at the rod's periphery than in the center with the effect of strongly edge-weighted beam energy distribution. Such a beam profile may not be desirable.

A second possible problem for Q-switched erbium lasers is the concentration-dependent upper state lifetime, whereby the lifetime is effectively shortened as the concentration increases. Quenching processes similar to those that populate the upper state can also depopulate it. In long pulse operation, energy is extracted continuously from the laser upper level and storage is not required. In this case some shortening of the lifetime is acceptable. By contrast, in Q-switched operation, energy must be stored in the upper state for a large fraction of the lamp pulse duration prior to Q-switching. Therefore, a reduced lifetime may impose limitations on the amount of stored energy that can be switched out of the system, translating to low output efficiencies in Q-switched mode.

Given these considerations, rods with lower erbium ion concentrations, preferably in the range of 25–40% would be more optimal for a laser with the output parameters considered in the present invention. The upper laser state storage efficiency will likely improve and beam spatial profiles that are more center-weighted will also result. With such concentrations, the pump absorption efficiency will not likely be overly compromised given the relatively low pulse energies required herein. We also note here that the lower erbium concentrations will be especially advantageous in a diode-pumped erbium laser, described further below in conjunction with FIG. 4.

The Q-switching to produce the short pulse is preferably carried out by electro-optical means using an active crystal 35, such as lithium niobate, inside Pockels cell 30. There are a number of issues associated with lithium niobate at this wavelength, notably the propensity for damage, both to the bulk material and to AR-coatings, due to absorption by $H_2O$ and $OH^-$ radicals in the 2.9-to-3.0 $\mu$m wavelength range and the need for high quarter-wave voltages to hold off the gain. For example, in the paper by H. J. Eichler et al., discussed above, it was noted that standard Pockels cells are not suitable for Q-switching an Er:YAG laser due to the high absorption and large voltages associated with this long wavelength. Indeed, coatings at 3 $\mu$m are not as well developed as those at 1 $\mu$m and there are very few suppliers of such coatings with acceptable performance.

This issue is addressed in our preferred approach by fabricating the crystal with Brewster faces, which eliminates the need for coatings. In addition, cavity and optical design parameters are carefully selected so as to keep the intracavity flux density low enough to avoid damage to the bulk material. The Brewster faces also serve to polarize the laser beam thereby eliminating additional optical elements in the cavity such as polarizers and wave plates. This is a consequence of the high index of lithium niobate (about 2.2), fortuitously coupled with the relatively low gain of the laser medium, whereby there is just enough polarization retardation and reflection to hold off the lasing without full quarter-wave rotation (see below). Another advantage associated with the preferred Brewster Q-switch implementation is that a Brewster-cut crystal with a rectangular cross section allows orientation of the electrodes such that the electric field can be placed along the short transverse dimension, thus minimizing the required voltage. The long dimension will then provide a symmetric aperture when the crystal is oriented at a Brewster angle to the beam. By selecting transverse dimensions just large enough to safely accommodate the beam diameter and coupled with the fact that the Er:YAG gain is not high at the stored energy densities of interest here, it was determined that a full quarter-wave rotation is not required to hold off lasing prior to Q-switching. Consequently, voltages in the 1.5–2.5 KV range were found to be adequate for the preferred 5 mm electrode spacing, which is substantially less than the 8 KV quoted in the Eichler reference as necessary for a Pockels cell containing lithium niobate.

Thus, the approach associated with the present invention is highly practical for an Er:YAG laser with modest energy output requirements. For example, in the case of the Q-switch, by seeking to minimize the crystal's transverse dimensions while also maximizing the crystal length/width aspect ratio, crystal dimensions of about 5 mm×10 mm×25 mm long were found to provide adequate hold-off at less than 2 KV voltage, yet with a clear aperture sufficient to intercept the beam from a flat-ended 3 mm Er:YAG rod preferred for the embodiment of FIG. 1. Brewster-cut lithium niobate crystals with these dimensions are readily procured from commercial sources.

Further indicated in FIG. 1, is a curved back mirror 40 coated for high reflection at the laser wavelength and a flat outcoupling mirror. This design is recognized as one of several possible standard resonator designs for a solid state laser, but in this particular case, it has the advantage that the Q-switch is located where the beam area is largest—and hence, the intracavity peak power density is lowest, thereby mitigating against the risk of damage to this sensitive component. The back mirror curvature is selected so as to optimize the resonator mode size for a given lamp input energy and associated power loading in the rod. In the example given earlier, a radius of about 1 m was found to yield reasonable $TEM_{00}$ mode size in the presence of thermal lensing. In alternative embodiments, a mirror with a shorter radius of curvature may be selected where it is determined that a smaller $TEM_{00}$ radius is preferred from the viewpoint of obtaining a smoother spatial beam profile by operating in a more highly multi-mode regime. Of course, such smoothing comes at the expense of increased output beam divergence and must therefore be carefully considered against constraints that may be imposed by each particular beam delivery system.

Figure 2:
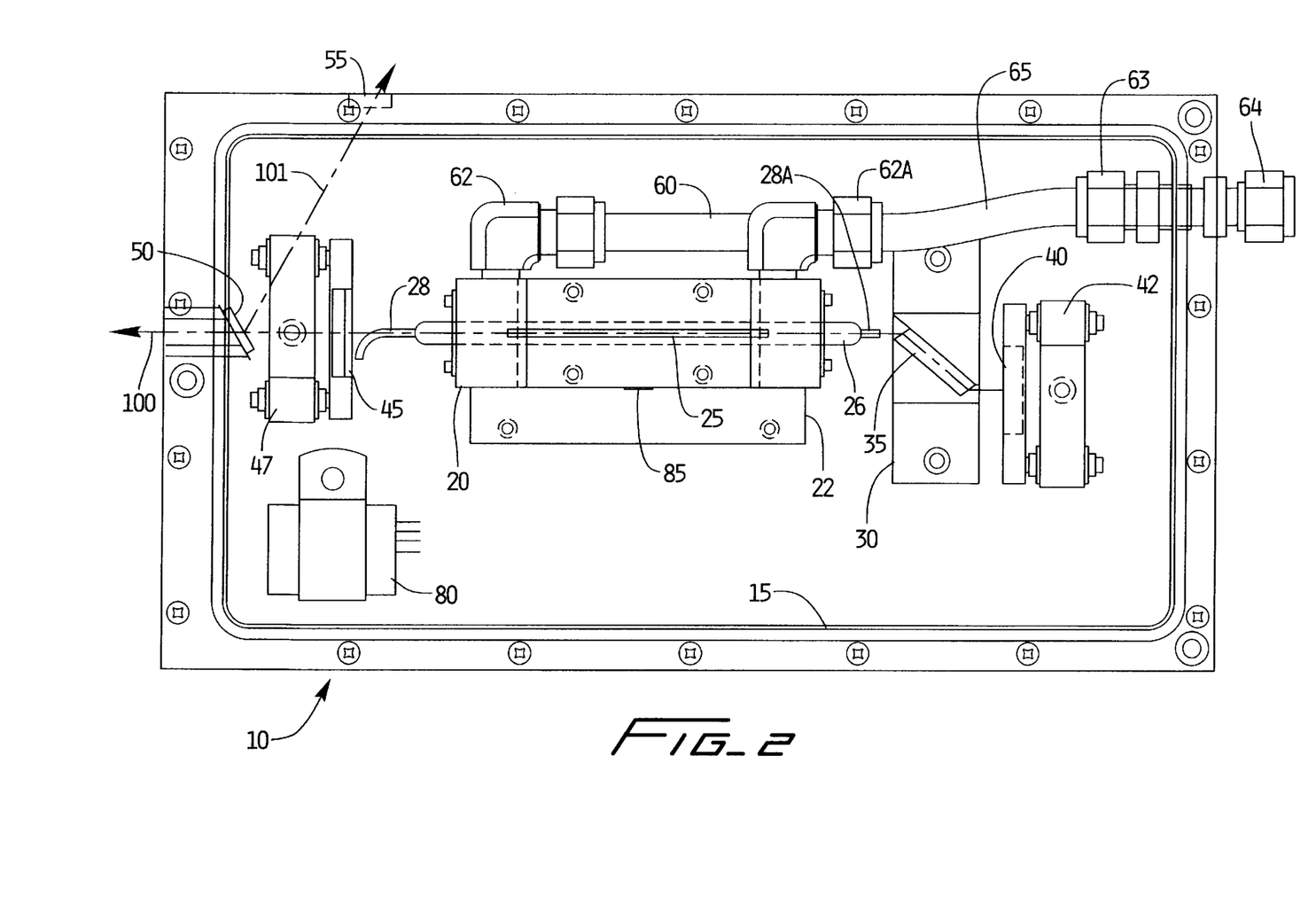
FIG. 2 is a layout (top view) showing an embodiment of a flashlamp-pumped Er:YAG laser device based on the preferred optical configuration of FIG. 1.

Referring now to FIG. 2, a detailed layout is shown representing an embodiment of a Q-switched Er:YAG laser device 10 based on the optical configuration of FIG. 1. The device is constructed according to principles of the present invention whereby the fewest optical elements are arranged to yield short resonator lengths and incorporating features that result in enhanced reliability at the requisite performance levels.

Accordingly, as shown in FIG. 2, the laser resonator cavity and all associated optics are contained in a hermetic enclosure 15 designed to minimize water contamination. In the preferred embodiment, the enclosure 15 is part of a hermetically sealed chassis 11 with provisions for flushing and containing an internal desiccant to further minimize the water content in the environment surrounding the laser optical surfaces.

As shown in FIG. 2, the Er:YAG rod 25 is contained in a water-cooled diffuse pump cavity 20, resting on an electrically insulating base plate 22. The rod is pumped with flashlamp 26 (indicated as behind the rod in this top view perspective), which preferably comprises a Xenon arc lamp capable of providing over 50 J energy at repetition rates of over 20 Hz. In the preferred embodiment, a diffuse cavity is selected to provide the best uniformity of illumination of the rod across the transverse aperture. A diffuse cavity also provides the advantage of presenting low inductance to the cooling loop, thereby allowing turbulent flow to cool larger volumes, which benefits operation at the higher end of the input power range. Diffuse cavities that use barium sulfate (BaS) as a high efficiency reflector (almost like silver) are preferred due to the demonstrated long life of this material. Ideally, the pump chamber imposes no excess length on the cavity dimension beyond that of the laser rod itself. The implementation described in FIG. 2 uses a diffuse BaS reflector in a water cooled cavity that combines efficient energy transfer from lamp to the rod with short on-axis dimension. In this implementation, the laser rod ends are directly accessible and form the limiting axial dimension. Such diffuse cavities are commercially available; for example, the Model 2400 Series cavity from IR Sources meets all the required specifications.

Selection of O-ring materials for sealing the rods in the pump bulk head 20 is yet another element where special care must be exercised for a short pulse mid-IR laser. In particular, it is critical to avoid materials that can outgas, melt along optical surfaces, or deposit on exposed optical surfaces including those of the rod and mirrors. For example, silicon, which has the advantage of low absorption of the pump light, may also present problems due to melting and outgassing. Viton is an alternative material which may have somewhat higher absorption but is not susceptible to melting and outgassing. We found that Viton is an acceptable sealant material, though it may still degrade over time, resulting in potential leaks. Yet another, possibly superior alternative is Kalrez which has better elasticity properties than silicon as well as low absorption properties. All of these and similar materials are commercially available.

Referring again to FIG. 2, the high reflectivity (HR) mirror 40 and the outcoupling mirror 45 are shown as held rigidly in place by standard mechanical mounts 42 and 47, respectively. It is noteworthy that while initial work was performed with discrete output coupling mirrors, a preferred approach would utilize an output coupling or a high reflectivity surface coated directly onto one of the rod ends. This eliminates one optic and mount, thus reducing resonator lengths by at least 1.5 inches. Such a shorter resonator would reduce the pulse duration by about 20%. An alternative option would involve moving the mirror 45 closer to the rod's end with a modified mount. Additional options for further shortening the resonator include the possibility of modifying the mechanical lay-out of the Q-switch by sliding it under the pump cavity 20, using again, appropriately designed mounts. This modification can reduce the resonator length by another 2 inches or so. Overall, we project that a cavity as short as 10 cm can be constructed, bringing the pulse duration down to 30 ns or less with only 25-to-30 J pump energy from the lamp. All such alternative constructions and various related mechanical or optical modifications, including ones not specifically mentioned here, fall under the scope of the present invention.

Further illustrated in FIG. 2 is the cooling line 60 including fittings 62 and 62A, coolant 65 and fittings 63, 64 inside and outside the cavity, respectively, that lead to a heat exchanger (not shown). A high voltage wire connection 85 to pump cavity 20 leads to a lamp trigger transformer 80 which is part of the power supply used to power the lamp and trigger the Q-switch. Electrical input to the lamp 26 is provided through the main current leads 28 and 28A which also connect to the power supply rack upon exiting through the back wall of the pump bulk head 20 (exit not shown in the perspective of FIG. 2). The erbium laser beam 100 is shown exiting through tilted window 50 with a small portion reflected through an energy monitor window 55 to an external detector (not shown). Other means of measuring the energy are possible as well, and are regarded as standard fixtures in the art of laser design and construction. In most of the applications contemplated in this invention, the beam 100 would be subsequently directed to some beam transfer optics (not shown), which form part of a larger beam delivery system to deliver the beam to the target tissue. In a preferred embodiment, the beam delivery system for a PRK application may include imaging and scanning means to allow selective removal of tissue at various points on the cornea thereby causing the cornea to change in a predictable and controlled manner. Such means were disclosed in our U.S. patent application Ser. No. 08/549,385, incorporated herein by reference, and are not considered critical to the present invention.

Figure 3:
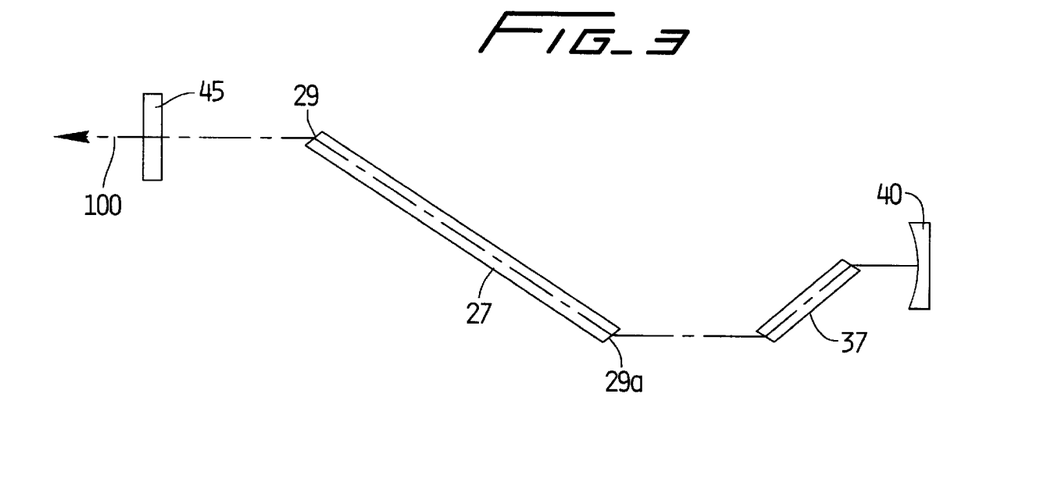
FIG. 3 is an optical schematic of an alternative embodiment of the Er:YAG laser, using a Brewster-cut laser rod and Q-switch medium.

In one alternative embodiment shown in FIG. 3, an optical configuration includes an erbium-doped rod 27 fabricated with Brewster-cut surfaces 29, 29a, instead of flat ends (see 24, 24a in FIG. 1). The Brewster surfaces 29, 29a can serve both to eliminate the need for AR-coating the rod and also to compress the beam dimension in one axis, thus allowing the use of a smaller Q-switch transverse dimension. As previously indicated, AR-coatings on the rod represent a potential source of damage due to residual absorption, particularly, at higher energy and/or peak power levels. With a Brewster cut rod, the laser beam is also more easily accommodated by a smaller sized Brewster cut Q-switch material and can be modulated at still lower voltages. The drawback is that an elliptically shaped beam and potentially higher order mode profiles are produced due to clipping of the beam by the rod's shorter dimension. This is because, in the absence of other intracavity apertures, the resultant elliptical aperture at the rod ends 29, 29a becomes the beam-defining aperture (unlike the Q-switch aperture which can be sized to accommodate a circular beam as described earlier). The elliptical beam cross sections thus generated may be more difficult to use and may also contain pronounced rectangular mode structure due to the spatial asymmetry. Moreover, the beam compression raises peak power loading at the critical Q-switch surface, thus adding another trade-off consideration for selecting the crystal's transverse dimension. Whether or not this alternative configuration is used depends on required power and energy levels. For the lowest energy outputs, such as in PRK applications, where energy/pulse levels of under 10 mJ/pulse are likely to suffice, the elimination of Er:YAG rod coatings may not be justified due to either damage or economic considerations, as the coatings may be sufficiently well developed to handle operation at these power levels. However, at higher energy levels (above 15–20 mJ), which may be desired for applications other than PRK, the Brewster configuration of FIG. 3 may present a potential advantage.

Ideally, the short pulse mid-IR source for PRK applications would also be scaleable to high repetition frequencies (over 50 Hz) without substantially increasing the expense and complexity of the device or compromising its reliability. This is an issue for Er:YAG lasers since strong thermal birefringence effects tend to limit the operation of the laser to pulse repetition frequencies of less than 20 Hz in a lamp-pumped system. However, with the help of diode arrays to provide the pump light instead of broad-band flashlamps it may be possible to extend the repetition rate of the erbium laser to over 30 Hz. What makes this option practical is the increasing availability, at reasonable cost, of high power, pulsed InGaAs diode arrays emitting in the 970 nm region where erbium ions have, the most absorption. A diode pumped Er:YAG system offers the potential for improved performance, due to more efficient absorption of light in the Er:YAG material as well as more efficient conversion of electrical input to pump light as compared to the flashlamp-pumped embodiment. Consequently, the same energy output from the laser can be produced at lower energy input—a definite advantage for a medical laser source. Also, because the pump energy is channeled more directly to the upper laser level, less of the pump energy appears as waste heat in the gain material. This reduced heat loading manifests itself in lower thermal lensing and thermally-induced depolarization loss (birefringence). These are otherwise the limiting factors in allowing scaling of a Q-switched Er:YAG to higher repetition rates (and average powers) as was discussed earlier in this specification. Diode arrays also exhibit much higher useful energy density as compared with flashlamps: thus, an Er:YAG laser capable of tens of millijoules output would require only a 1–2 cm long diode array. The pumped laser rod can be correspondingly shortened which is a very important consideration when aiming to produce the shortest possible pulses, a key aspect of the present invention. Note that even in the most optimized lamp-pumped case, the practical resonator length is dominated by the rod length, which limited the minimum pulse duration that could be achieved in that case.

Figure 4:
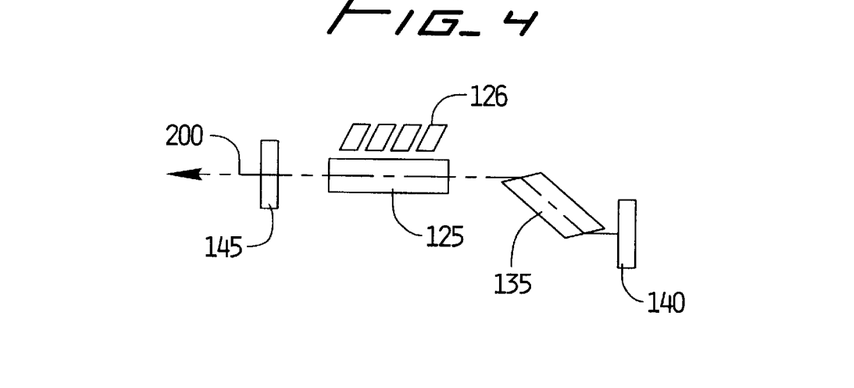
FIG. 4 is an optical schematic of a preferred embodiment of a diode side-pumped Er:YAG laser configuration.

Accordingly, it is shown in FIG. 4 that an alternative embodiment of the Q-switched erbium laser comprises, as a key element, a short Er:YAG rod 125 pumped transversely by a diode array 126, the wavelength of which is tuned to a maximum in the gain material absorption, which is around 970 nm in the case of Er:YAG. The diode array pump will preferably comprise several InGaAs diode arrays, each consisting of a number of bars, similar to what is commercially available with the more advanced GaAlAs diodes used to pump neodymium lasers. The transverse coupling configuration may consist of any one of several known arrangements already applied successfully to diode side-pumping of the more standard Nd:YAG lasers and all such specific methods and techniques fall within the scope of the present invention. In one preferred embodiment, an erbium-doped rod of only 1 cm in length and 2–3 mm in diameter will be sufficient to produce over 5 mJ energy output in a Q-switched mode, at slope efficiencies in excess of 0.1%, depending on the details of the resonator design. A very short resonator of less than 5 cm in length may be feasible in this case, assuming a miniaturized Q-switch is available, leading to pulse durations of well under 30 ns. We believe that a diode-pumped erbium-doped laser with the said output properties may be fabricated in the near-term based on recent advances in the state-of-the-art of InGaAs diode array technology.

It is to be understood in FIG. 4 that the mirrors 140 and 145 represent generic optics and that one or the other may be substituted by coatings directly applied to the rod's ends, depending on the specifics of the resonator configuration. Such a semi-monolithic configuration may be desirable in the interest of achieving lowest loss and shortest resonator lengths. Also in FIG. 4, the Q-switch 135 is shown at a Brewster angle; however, a flat-ended, straight-through Q-switch may be an acceptable alternative in this more efficient diode pumped laser due to the lower circulating intracavity power which may be tolerated by the crystal's AR coatings without damage. Of course, a polarizing element will then have to be inserted into the cavity, but the losses associated with such an element may be acceptable in this case.

While performance under diode pumping is expected to be generally superior to that of a lamp-pumped case, a single Er:YAG rod is still constrained to 30–40 Hz maximum pulse repetition frequency due to the long lifetime of the lower laser state. Beyond this repetition rate, population build-up occurs in the lower state followed by termination of laser action.

A method to overcome this inherent limitation is to divide the gain stage into two sections, each pumped individually by InGaAs diode bars. Since thermal distortion is one of the features restricting higher repetition rates to be obtained, a polarization rotator and a compensating lens may be placed between the two sections of gain media to provide correction of this distortion. By using two identically pumped sections, each fired at the maximum rate of 30–40 Hz with a delay of ½ the inter-pulse temporal interval, the overall repetition rate can be effectively doubled. This is possible because the unpumped gain material sections are essentially transparent to the laser light and therefore laser gain and stored energy are available at twice the rate of each section individually, i.e. about 60–80 Hz. With careful design, the total length of two sections, including corrective optics in-between, can be less than one third of the length of a typical lamp pumped rod. With attention to mounting and minimization of intra-component spacing an overall resonator length as short as 5 cm is attainable. This is approximately one half the length of a fully optimized lamp-pumped configuration, including the preferred features of a semi-monolithic rod with one face comprising the outcoupling mirror and a better mechanical packaging of the laser cavity and Q-switch components. Since the pulse width is nearly linearly dependent on the cavity length, we estimate that pulse widths on the order of 20 ns should be attainable from such a high repetition rate diode—pumped Er:YAG laser.

Yet another alternative configuration of a diode pumped erbium laser involves longitudinal pumping of the laser rod. This arrangement has an advantage over transverse pumping in that rod diameters can be kept small, leading to better energy storage density and hence gain. Such a configuration is also extremely simple and has the further advantage of providing a superior match to single transverse mode operation because of favorable pump and mode volume overlap characteristics. The main issue with end-pumping is the availability of diode lasers with the requisite power concentrated in a sufficiently small area to allow effective coupling to the rod. A tightly-packed fiber bundle may provide one effective means to scale the pump power by combining radiation delivered from several individual diode pump lasers.

Figure 5:
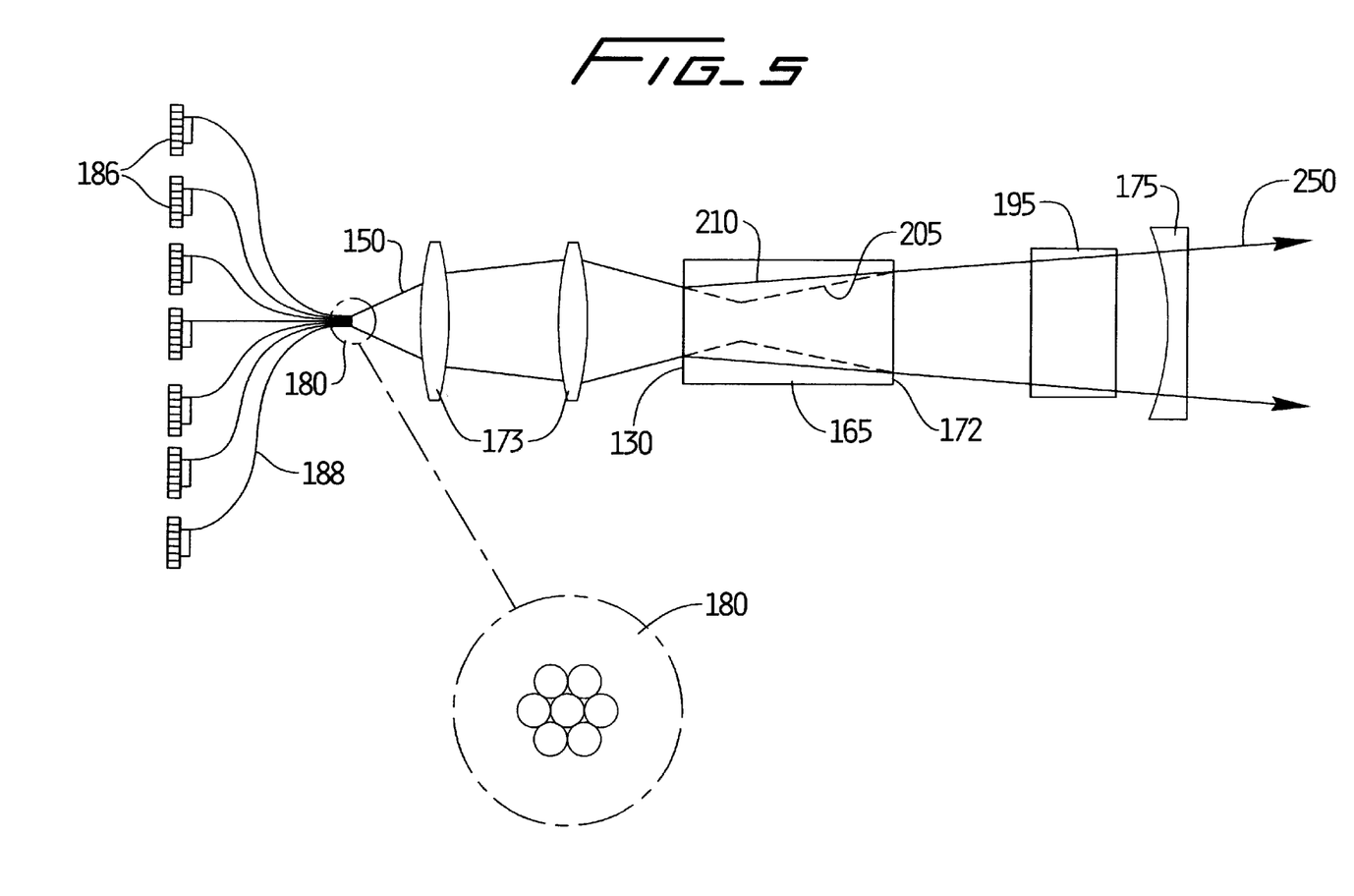
FIG. 5 is a schematic of another preferred embodiment of a fiber coupled diode end-pumped Er:YAG laser.

An arrangement based on this approach was successfully used to scale the output power from a diode end-pumped Nd:YAG laser—see J. Berger, et al., Opt. lett., 13, pp. 306 (1988). To indicate the key elements and benefits of such a method when applied to the case of an erbium-doped laser, there is shown in FIG. 5 a schematic of a fiber-bundle coupled, diode-pumped laser modified from the above reference. As indicated in the figure, the light from seven diode arrays 186 are each coupled into fibers 188, which are tightly bundled into an array 180. The light 150 from the array 180 is collimated and imaged unto a rod 165 using coupling lenses 173. The end 170 of rod 165 is preferably coated to reflect 100% of the light at the lasing wavelength while transmitting most of the diode pump wavelength. Also shown is a Q-switch 195 (which may be brewster-cut or flat-ended with AR coating) and partially transmitting mirror 175, which serves as outcoupler for short-pulse, mid-IR beam 250. Further indicated in FIG. 5 is the high degree of overlap between pump mode 205 and the laser mode 210. This overlap results in long interaction lengths leading to a maximally efficient laser. Furthermore, the longitudinal arrangement is especially well matched to operate in the fundamental $TEM_{00}$ mode due to the center-weighting of the pump absorption. Therefore, in the case of the low gain erbium laser, diode end-pumping may be the only efficient means of generating a 3 micron beam in a single transverse mode.

Figure 5A:
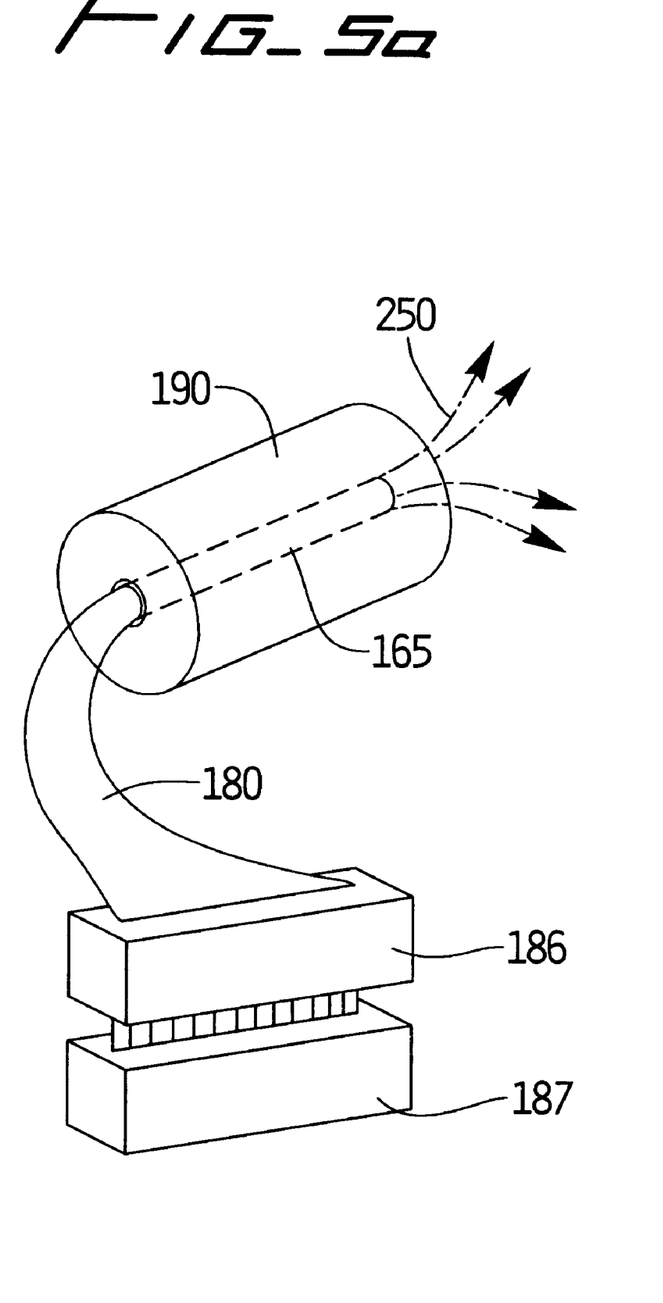
FIG. 5a is a perspective view of an alternative fiber bundle coupling to the laser rod.

FIG. 5a shows an alternative butt-coupling method of the light from diodes 186 (with associated control electronics 187) to rod 165. For illustrative purposes, also shown in FIG. 5a is a copper sleeve 190 which acts as a heat-sink to conduct the waste heat from the rod. Thus, for the relatively low power application of concern to the present invention, water cooling may not be necessary except at the highest repetition frequencies, resulting in a very simple and compact package.

Compared with the preferred embodiment of a transversely-pumped erbium laser, a longitudinally pumped arrangement may have a slight disadvantage in terms of achieving the shortest possible pulse length. This is because the rod length has to be selected to maximize pump absorption; consequently, rod lengths of at least 2 cm may be necessary to fully absorb the pump light, assuming rods with 50% concentration. On the other hand, the higher gains that can be realized with an end-pumped geometry may compensate for the somewhat longer resonator lengths, leading again to pulse durations in the 20–30 ns range.

Embodiments such as the ones indicated in FIGS. 5 and 5a represent only some of the possible techniques to achieve end-pumping of erbium lasers. Alternative embodiments include utilization of specially designed imaging microlenses and other similar techniques recently used in successful implementations of diode end-pumped neodymium-doped lasers.

Among other advantages of diode end-pumped lasers with multiple diode arrays is the enhanced reliability features due to graceful degradation of the diodes. Another advantage is the possibility of parallel combining the output from one or more lasers to scale the overall repetition rates to over 60 Hz. This approach is made feasible by the highly compact nature of the diode end-pumped laser. Still another advantage is the decoupling of the pump source from the laser, which is a decided advantage in the crowded operating room environment.

It is to be understood that the embodiments and variations shown and described herein are merely illustrative of the principles of this invention and that various modifications may be implemented by those skilled in the art without departing from the scope and spirit of the invention.

In particular, the specific Q-switch material can be altered by selecting an alternative birefringent medium such as Rubidium Titanyl Arsenate (RTA), Cesium Titanyl Arsenate (CTA), or Potassium Titanyl Phosphate (KTP). High damage thresholds for these materials have been reported, and they are currently being researched for potential use as Q-switches. One drawback to using these materials is that, unlike lithium niobate, they are biaxial, and will require specially designed temperature control cells. Also, the phase retardation of each material is different and each would need to be separately calibrated for the proper operating range of voltage.

In addition, the specific wavelength of the output beam can be altered by selecting an alternative host for the erbium ion such as Yttrium Aluminum Oxide, $YAlO_3$ (YALO), Yttrium Lithium Fluoride (YLF) or yttrium-scandium gallium garnet (YSGG). The corresponding wavelength for the erbium ion ranges from 2.79 $\mu$m to 3.02 $\mu$m. The possibility of utilizing one of several alternative erbium-doped crystals is a potentially useful feature in the surgical context since absorption properties may differ among different types of tissues and, for example, even within the same tissue, as a function of temperature. Hence a variation of wavelength could allow matching to the optimal absorption desired for a given procedure, thus enlarging the scope and utility of the erbium laser source. The limitation on the wavelength range that can be so obtained is determined by the availability of a particular laser rod with the requisite quality and size.

Still another alternative laser medium for 3 micron applications is based on the holmium ($Ho^{3+}$) ion, which in certain host materials, such as YALO, can be made to lase at several wavelengths between 2.8 and 2.92 $\mu$m. See, for example, S. R. Bowman, et al. in IEEF J. Quantum Electron, 26, p. 403 (1990). It is to be noted that the holmium ion transitions are fundamentally different than those of erbium, in that the relevant lower laser level is an excited state. Special care must also be taken to avoid self-termination due to the long life of this state, but under the right kind of pumping conditions—preferably resonant with a particular absorption line—population inversion can be created and maintained. The transitions of interest are compatible with short pulse operation, and one of several resonator design options based on principles discussed above will likely be appropriate for this alternative class of holmium-doped lasers. Therefore, all such combinations of known materials and dopants, which can directly produce wavelengths ranging from 2.79 to 3.02 microns in a short pulse mode fall within the scope of the present invention.

We claim:

1. A mid-infrared laser system for performing a laser surgical procedure on a tissue, said system comprising:
   a laser resonator cavity;
   a laser rod within said cavity operatively configured and adapted to produce a laser beam having a wavelength in the mid-infrared range, from about 2.5 to about 4.0 um, and which wavelength corresponds approximately to an absorption peak of said tissue, said laser rod being pumped by a pump source; and an electro-optical Q-switch to control the oscillation of said laser beam within the resonator cavity to produce pulses of said laser beam, wherein the length of said resonator cavity is less than about 30 cm and sufficiently short to provide pulse durations shorter than 50 ns.

2. The laser system according to claim 1, wherein said laser rod is erbium-doped.

3. The laser system according to claim 2, wherein the erbium concentration of said rod is at about a 25–40% doping level.

4. The laser system according to claim 1, wherein the host of the active ion of said laser rod is comprised of YALO, YLF, YSGG or YAG.

5. The laser system according to claim 1, further comprising means for directing said laser beam onto said tissue to remove portions of said tissue primarily by a photo-mechanical ablation process.

6. The laser system according to claim 1, wherein an output coupling surface is coated onto one end of said laser rod.

7. The laser system according to claim 1, wherein said pump source is a flashlamp.

8. The laser system according to claim 1, wherein said pump source is a diode array.

9. The laser system according to claim 8, wherein said diode array pumps said laser rod in a side-pumped configuration.

10. The laser system according to claim 8, wherein said diode array pumps said laser rod in an end-pumped configuration.

11. The laser system according to claim 8, whereby an overall repetition rate of at least 20 Hz is achieved.

12. The laser system according to claim 1, wherein said pulses are produced at a repetition rate of at approximately 10 Hz.

13. The laser system according to claim 1, wherein said Q-switch is comprised of lithium niobate.

14. The laser system according to claim 1, wherein said surgical procedure is a corneal ablation procedure.

15. The laser system according to claim 14, wherein said corneal ablation procedure is based on a photospallation mechanism.

16. The laser system according to claim 14, wherein the fluence onto the eye is between 50 mJ/cm$^2$ and 200 mJ/cm$^2$.

17. The laser system according to claim 1, wherein said surgical procedure is an endoscopic procedure or a microsurgical procedure.

18. The laser system according to claim 1, wherein a high reflecting surface is coated onto one end of said laser rod.

19. The laser system according to claim 1, wherein the resonator cavity is less than about 20 cm.

20. The laser system according to claim 1, wherein the hold-off voltage for producing the beam is less than about 2.5 KV.

21. The laser system according to claim 1, wherein the host of the active ion of said laser rod is selected from the group consisting of: garnet, an oxide or a fluoride crystal.

22. A mid-infrared laser system for performing a laser surgical procedure on a tissue, said system comprising:

a laser resonator cavity;

a laser rod within said cavity operatively configured and adapted to produce a laser beam having a wavelength in the mid-infrared range approximately between about 2.7 and about 3.0, said laser rod being pumped by a pump source; and an electro-optical Q-switch to control the oscillation of said laser beam within the resonator cavity to produce pulses of said laser beam, wherein the length of said resonator cavity is less than about 30 cm and sufficiently short to provide pulse durations shorter than 50 ns.

23. The laser system according to claim 22, wherein the resonator cavity is less than about 20 cm.

24. The laser system according to claim 22, wherein the hold-off voltage for producing the beam is less than about 2.5 KV.

25. A method for performing a laser surgical procedure on a tissue, said method comprising the steps of:

generating a laser beam in the mid-infrared range approximately between 2.79 and 3.02 µm;

oscillating said beam in a resonator cavity; and controlling said oscillation using a Q-switch to produce pulses of said laser beam, wherein the length of said resonator cavity is sufficiently short to provide pulse durations shorter than 50 ns.

26. A method for performing a laser surgical procedure on a tissue, said method comprising the steps of:

generating a laser beam in the mid-infrared range corresponding approximately to an absorption peak of said tissue;

oscillating said beam in a resonator cavity; and controlling said oscillation using a Q-switch to produce pulses of said laser beam, wherein the length of said resonator cavity is sufficiently short to provide pulse durations shorter than 50 ns.

27. A method for removing corneal tissue from an eye of a patient, said method comprising the steps of:

generating a laser beam in the mid-infrared range approximately to an absorption peak of said corneal tissue;

oscillating said beam in a resonator cavity;

controlling said oscillation using a Q-switch to produce pulses of said laser beam, wherein the length of said resonator cavity is sufficiently short to provide pulse durations shorter than 50 ns; and directing said beam across an area of said corneal tissue in a predefined pattern to remove portions of said corneal tissue primarily by a photo-mechanical ablation process.

28. A mid-infrared laser system for removing corneal tissue from any eye of a patient, said system comprising:

a laser resonator cavity;

a laser rod within said cavity operatively configured and adapted to produce a laser beam having a wavelength in the mid-infrared range corresponding approximately to an absorption peak of said corneal tissue, said laser rod being pumped by a pump source;

an electro-optical Q-switch to control the oscillation of said laser beam within the resonator cavity to produce pulses of said laser beam, wherein the length of said resonator cavity is sufficiently short to provide pulse durations shorter than 50 ns; and means for directing said laser beam onto said eye in a pre-defined pattern to remove portions of said corneal tissue primarily by a photo-mechanical ablation process.

29. The laser system according to claim 28, wherein the resonator cavity is less than about 30 cm.

30. The laser system according to claim 28, wherein the resonator cavity is less than about 20 cm.

31. The laser system according to claim 28, wherein the hold-off voltage for producing the beam is less than about 2.5 KV.

32. A mid-infrared laser system for performing a laser surgical procedure on a tissue, said system comprising:

a laser resonator cavity;

a laser rod within said cavity, said laser rod being pumped by a pump source to produce a laser beam having a wavelength in the mid-infrared range corresponding approximately to an absorption peak of said tissue; and a Q-switch to control the oscillation of said laser beam within the resonator cavity to produce pulses of said laser beam, wherein the length of said resonator cavity is sufficiently short to provide pulse durations shorter than 50 ns and wherein the ends of said laser rod are cut at the Brewster angle.

33. A mid-infrared laser system for performing a laser surgical procedure on a tissue, said system comprising:

a laser resonator cavity;

a laser rod within said cavity, said laser rod being pumped by a pump source to produce a laser beam having a wavelength in the mid-infrared range corresponding approximately to an absorption peak of said tissue; and a Q-switch to control the oscillation of said laser beam within the resonator cavity to produce pulses of said laser beam, wherein the length of said resonator cavity is less than about 30 cm and sufficiently short to provide pulse durations shorter than 50 ns and wherein the ends of said Q-switch material are cut at the Brewster angle.

34. The laser system according to claim 33, wherein the resonator cavity is less than about 20 cm.

35. A mid-infrared laser system for performing a laser surgical procedure on a tissue, said system comprising:

a laser resonator cavity;

a laser rod within said cavity, said laser rod being pumped by a pump source to produce a laser beam having a wavelength in the mid-infrared range corresponding approximately to an absorption peak of said tissue; and a Q-switch to control the oscillation of said laser beam within the resonator cavity to produce pulses of said laser beam, wherein the length of said resonator cavity is sufficiently short to provide pulse durations shorter than 50 ns and wherein said pump source is a diode array, and wherein said diode array pumps said laser rod in an end-pumped configuration, and wherein said laser rod is comprised of a plurality of sections N, each end-pumped individually, whereby an overall repetition rate of at least 20 Hz*N is achieved in a laser beam combined by a beam delivery system.

36. A method for performing a laser surgical procedure on a tissue, said method comprising the steps of:

generating a laser beam in the mid-infrared range corresponding approximately to an absorption peak of said tissue using an erbium-doped laser rod;

oscillating said beam in a resonator cavity; and controlling said oscillation using a Q-switch to produce pulses of said laser beam, wherein the length of said resonator cavity is less than about 30 cm and sufficiently short to provide pulse durations shorter than 50 ns and wherein said laser rod is erbium-doped.

37. The laser system according to claim 36, wherein the resonator cavity is less than about 20 cm.

38. A method for performing a laser surgical procedure on a tissue, said method comprising the steps of:

generating a laser beam in the mid-infrared range corresponding approximately to an absorption peak of said tissue using an erbium-doped laser rod;

oscillating said beam in a resonator cavity; and controlling said oscillation using a Q-switch to produce pulses of said laser beam, wherein the length of said resonator cavity is sufficiently short to provide pulse durations shorter than 50 ns;

directing said laser beam onto said tissue to remove portions of said tissue primarily by a photo-mechanical ablation process.

39. A method for performing a laser surgical procedure on a tissue, said method comprising the steps of:

generating a laser beam in the mid-infrared range corresponding approximately to an absorption peak of said tissue using an erbium-doped laser rod;

oscillating said beam in a resonator cavity; and controlling said oscillation using a Q-switch to produce pulses of said laser beam, wherein the length of said resonator cavity is sufficiently short to provide pulse durations shorter than 50 ns and the pulses are produced at a repetition rate of at least approximately 10 Hz.

40. A method for performing a laser surgical procedure on a tissue, said procedure being selected from the group consisting of: a corneal ablation procedure, an endoscopic procedure and a micro-ocular procedure, said method comprising the steps of:

generating a laser beam in the mid-infrared range corresponding approximately to an absorption peak of said tissue using an erbium-doped laser rod;

oscillating said beam in a resonator cavity; and controlling said oscillation using a Q-switch to produce pulses of said laser beam, wherein the length of said resonator cavity is less than about 30 cm and sufficiently short to provide pulse durations shorter than 50 ns.

41. The laser system according to claim 40, wherein the resonator cavity is less than about 20 cm.

42. A method for performing a corneal ablation procedure based on a photospallation mechanism, said method comprising the steps of:

generating a laser beam in the mid-infrared range corresponding approximately to an absorption peak of said tissue using an erbium-doped laser rod;

oscillating said beam in a resonator cavity; and controlling said oscillation using a Q-switch to produce pulses of said laser beam, wherein the length of said resonator cavity is less than about 30 cm and sufficiently short to provide pulse durations shorter than 50 ns.

43. The laser system according to claim 42, wherein the resonator cavity is less than about 20 cm.

44. A method for performing a corneal ablation procedure based on a photospallation mechanism, wherein the fluence onto the eye is between 50 mJ/cm$^2$ and 200 mJ/cm$^2$, said method comprising the steps of:

generating a laser beam in the mid-infrared range corresponding approximately to an absorption peak of said tissue using an erbium-doped laser rod;

oscillating said beam in a resonator cavity; and controlling said oscillation using a Q-switch to produce pulses of said laser beam, wherein the length of said resonator cavity is sufficiently short to provide pulse durations shorter than 50 ns.

45. A method for performing a laser surgical procedure on a tissue, said method comprising the steps of:
- generating a laser beam in the mid-infrared range corresponding approximately to an absorption peak of said tissue using a laser rod;
- oscillating said beam in a resonator cavity; and controlling said oscillation using a Q-switch to produce pulses of said laser beam; wherein the length of said resonator cavity is sufficiently short to provide pulse durations shorter than 50 ns and the hold-off voltage for generating the laser beam is less than about 2.5 KV.

46. A mid-infrared laser system for performing a laser surgical procedure on a tissue, said system comprising:
- a laser resonator cavity;
- a laser rod within said cavity, said laser rod being pumped by a pump source to produce a laser beam having a wavelength in the mid-infrared range corresponding approximately to an absorption peak of said tissue; and
- a Q-switch to control the oscillation of said laser beam within the resonator cavity to produce pulses of said laser beam, wherein the length of said resonator cavity is sufficiently short to provide pulse durations shorter than 50 ns and wherein the hold-off voltage for generating the laser beam is less than about 2.5 KV.

47. A mid-infrared laser system for performing a laser surgical procedure on a tissue, said system comprising:
- a laser resonator cavity;
- a laser rod within said cavity, said laser rod being pumped by a pump source to produce a laser beam having a wavelength in the mid-infrared range corresponding approximately to an absorption peak of said tissue; and
- a Q-switch to control the oscillation of said laser beam within the resonator cavity to produce pulses of said laser beam, wherein the length of said resonator cavity is sufficiently short to provide pulse durations shorter than 50 ns and wherein pulses are produced at a repetition rate of at least approximately 10 Hz.

48. A mid-infrared laser system for performing a laser surgical procedure on a tissue, said system comprising:
- a laser resonator cavity;
- a laser rod within said cavity, said laser rod being pumped by a pump source to produce a laser beam having a wavelength in the mid-infrared range corresponding approximately to an absorption peak of said tissue; and
- a Q-switch to control the oscillation of said laser beam within the resonator cavity to produce pulses of said laser beam, wherein the length of said resonator cavity is sufficiently short to provide pulse durations shorter than 50 ns and wherein said pump source is a diode array.

49. A method for performing a corneal ablation procedure based on a photospallation mechanism, wherein the fluence onto the eye is between 50 mJ/cm$^2$ and 200 mJ/cm$^2$, said method comprising the steps of:
- generating a laser beam in the mid-infrared range corresponding approximately to an absorption peak of said tissue using an erbium-doped laser rod;
- oscillating said beam in a resonator cavity; and controlling said oscillation using a Q-switch to produce pulses of said laser beam, wherein the length of said resonator cavity is sufficiently short to provide pulse durations shorter than 70 ns.

50. A method for performing a corneal ablation procedure based on a photospallation mechanism, wherein the threshold fluence for obtaining ablation less than about 100 mJ/cm$^2$, said method comprising the steps of:
- generating a laser beam in the mid-infrared range corresponding approximately to an absorption peak of said tissue using an erbium-doped laser rod;
- oscillating said beam in a resonator cavity; and controlling said oscillation using a Q-switch to produce pulses of said laser beam, wherein the length of said resonator cavity is sufficiently short to provide pulse durations shorter than 70 ns.

51. A method for performing a corneal ablation procedure based on a photospallation mechanism, wherein the thermal damage zone generated by the ablation procedure is less than 2 um, said method comprising the steps of:
- generating a laser beam in the mid-infrared range corresponding approximately to an absorption peak of said tissue using an erbium-doped laser rod;
- oscillating said beam in a resonator cavity; and controlling said oscillation using a Q-switch to produce pulses of said laser beam, wherein the length of said resonator cavity is sufficiently short to provide pulse durations shorter than 70 ns.

* * * * *